(12) United States Patent
Takada et al.

(10) Patent No.: US 10,815,174 B2
(45) Date of Patent: Oct. 27, 2020

(54) STORAGE CONTAINER AND STORAGE METHOD OF Z-1-CHLORO-3,3,3-TRIFLUOROPROPENE

(71) Applicant: CENTRAL GLASS COMPANY, LIMITED, Yamaguchi (JP)

(72) Inventors: Naoto Takada, Kanagawa (JP); Masahiko Tani, Kanagawa (JP); Hideaki Imura, Saitama (JP); Koji Ueda, Saitama (JP); Yoshio Nishiguchi, Saitama (JP); Fuyuhiko Sakyu, Saitama (JP)

(73) Assignee: CENTRAL GLASS COMPANY, LIMITED, Ube, Yamaguchi (JP)

( * ) Notice: Subject to any disclaimer, the term of this patent is extended or adjusted under 35 U.S.C. 154(b) by 0 days.

(21) Appl. No.: 16/264,457

(22) Filed: Jan. 31, 2019

(65) Prior Publication Data

US 2019/0169103 A1 Jun. 6, 2019

Related U.S. Application Data

(63) Continuation of application No. PCT/JP2017/026435, filed on Jul. 21, 2017.

(30) Foreign Application Priority Data

Aug. 5, 2016 (JP) .................................. 2016-154429

(51) Int. Cl.
*C07C 21/18* (2006.01)
*B65D 25/14* (2006.01)
*B65D 85/00* (2006.01)

(52) U.S. Cl.
CPC .............. *C07C 21/18* (2013.01); *B65D 25/14* (2013.01); *B65D 85/70* (2013.01)

(58) Field of Classification Search
None
See application file for complete search history.

(56) References Cited

U.S. PATENT DOCUMENTS

| | | | |
|---|---|---|---|
| 8,877,989 B2 | 11/2014 | Nishiguchi et al. | |
| 2003/0028057 A1 | 2/2003 | Owens et al. | |
| 2011/0001080 A1* | 1/2011 | Van Horn | C09K 5/044 252/68 |
| 2013/0090280 A1 | 4/2013 | Basu et al. | |
| 2013/0162363 A1 | 6/2013 | Han et al. | |
| 2013/0165363 A1 | 6/2013 | Decaire et al. | |
| 2014/0178312 A1* | 6/2014 | Basu | C09K 3/30 424/45 |
| 2014/0336424 A1 | 11/2014 | Okamoto et al. | |
| 2014/0339321 A1 | 11/2014 | Ryokawa et al. | |
| 2015/0011805 A1 | 1/2015 | Okamoto et al. | |
| 2016/0272560 A1* | 9/2016 | Chiu | C07C 17/389 |

FOREIGN PATENT DOCUMENTS

| | | | |
|---|---|---|---|
| CN | 86101055 A | 10/1987 | |
| CN | 101808966 A | 8/2010 | |
| CN | 103097325 A | 5/2013 | |
| CN | 103946198 A | 7/2014 | |
| CN | 103958658 A | 7/2014 | |
| CN | 104093791 A | 10/2014 | |
| JP | 2010-531926 A | 9/2010 | |
| JP | 2013103890 A | 5/2013 | |
| JP | 2014-529656 A | 11/2014 | |
| JP | 2015-003765 A | 1/2015 | |
| WO | 2009/114397 A2 | 9/2009 | |
| WO | 2013/028943 A2 | 2/2013 | |
| WO | WO-2018075864 A1 * | 4/2018 | ........... B65D 83/752 |

OTHER PUBLICATIONS

Climalife "R-1233zd Trans-1-chloro-3,3,3-trifluoroprop-1-ene" 2014, pp. 1-2 (Year: 2014).*
English translation of Written Opinion of the International Search Authority dated Oct. 3, 2017 for the corresponding PCT application No. PCT/JP2017/026435.
Written Opinion of the International Search Authority dated Oct. 3, 2017 for the PCT application No. PCT/ JP2017/026435.
International Search Report dated Oct. 3, 2017 for the PCT application No. PCT/JP2017/026435, with English translation.
Chinese Office Action dated Oct. 30, 2019 for corresponding Chinese Application No. 201780041780.6, with Partial English translation.
Chinese Office Action for corresponding Chinese application No. 201780041780.6 dated May 11, 2020, references with Partial English Translation.
Office Action issued for corresponding Japanese Patent Application No. 2018-531835 dated Feb. 18, 2020, along with an English translation.
Office Action issued for corresponding Japanese Patent Application No. 2018-531835 dated Jul. 7, 2020 along with a partial English machine translation.

(Continued)

*Primary Examiner* — Medhanit W Bahta
(74) *Attorney, Agent, or Firm* — Hauptman Ham, LLP

(57) ABSTRACT

A storage method of HCFO-1233zd (Z) according to an embodiment of the present invention, includes using a storage container having a liquid-contact portion thereof. The liquid-contact portion is formed of a material selected from the group consisting of epoxy-phenolic resin, phenolic resin, phenolic-butyral resin, stainless steel, iron phosphate, zinc phosphate and glass.

16 Claims, No Drawings

(56) References Cited

OTHER PUBLICATIONS

Extended European Search Report issued for corresponding European Patent Application No. 17836767.8 dated Jul. 22, 2020.
Synquest Laboratories, "SynQuest Labs—for Fluoro's, Gases, & Monomers", Synquest Fluorochemicals Catalog, Jan. 1, 2003, p. 98.
Lisa Stojanovich, "The Purpose of a Steel Drum Lining—Drum It Up!", Skolnik, Jan. 10, 2014, <https://www.skolnik.com/blog/the-purpose-of-a-drum-lining/> (retrieved Mar. 18, 2020).

\* cited by examiner

STORAGE CONTAINER AND STORAGE METHOD OF Z-1-CHLORO-3,3,3-TRIFLUOROPROPENE

CROSS REFERENCE TO RELATED APPLICATIONS

This application is based upon and claims the benefit of priority from the prior Japanese Patent Application No. 2016-154429, filed on Aug. 5, 2016 and PCT International Application No. PCT/JP2017/026435, filed on Jul. 21, 2017, the entire contents of which are incorporated herein by reference.

FIELD

The present invention relates a storage container and a storage method of Z-1-chloro-3,3,3-trifluoropropene.

BACKGROUND

In order to prevent global warming and ozone layer depletion, various Freon substitutes have been proposed so far. In order to protect the ozone layer, hydrofluorocarbons (HFCs), which do not generate chlorine radicals causing ozone layer depletion, spread widely. However, HFCs generally have a long atmospheric lifetime and have a significant influence on global environments, for example, cause global warming or the like. In the commercial markets, regulations on HFCs are being made progressively. As a substitute for HFCs, hydrofluoroolefin (HFO), which includes a double bond in a molecule and has a short atmospheric lifetime, and hydrochlorofluoroolefin (HCFO), which is obtained by incorporation of chlorine into HFO, have been introduced.

HCFO has a low global warming potential, is relatively low in toxicity, and is highly compatible. HCFO also has a higher boiling point than that of HFO, and specifically has an advantage of being capable to form a high density foam as a foaming agent.

1-chloro-3,3,3-trifluoropropene (HCFO-1233zd) is available in geometrical isomers of trans isomer (E isomer) and cis isomer (Z isomer), which are respectively referred to as HCFO-1233zd (E) and HCFO-1233zd (Z). HCFO-1233zd (E) is now commercially produced as a next-generation foaming agent. For HCFO-1233zd (Z), uses as a solvent and a detergent have been proposed (Japanese Laid-Open Patent Publication No. 2013-103890).

HCFO-1233zd (Z) is known to cause resin erosion due to its high solubility, such as acrylonitrile-butadiene-styrene (ABS) plastics, high impact styrene black, acrylic resin, polycarbonate and the like (PCT Japanese National-Phase Laid-Open Patent Publication No. 2014-529656).

SUMMARY

The present invention has an object of providing a storage container and a storage method that maintain the quality of Z-1-chloro-3,3,3-trifluoropropene (abbreviation: HCFO-1233zd (Z)) as a solvent or a detergent, and are usable to store and transport Z-1-chloro-3,3,3-trifluoropropene safely and stably at low cost.

A storage container for HCFO-1233zd (Z) according to an embodiment of the present invention, to be filled with HCFO-1233zd (Z), includes a material of at least a liquid-contact portion thereof. The material is selected from the group consisting of epoxy-phenolic resin, phenolic resin, phenolic-butyral resin, stainless steel, iron phosphate, zinc phosphate and glass.

The material of the liquid-contact portion may be selected from the group consisting of phenolic resin, phenolic-butyral resin, iron phosphate and zinc phosphate.

The material of the liquid-contact portion may be selected from the group consisting of iron phosphate and zinc phosphate.

The storage container for HCFO-1233zd (Z) may be sealable.

A storage method of HCFO-1233zd (Z) according to an embodiment of the present invention, includes using a storage container having a liquid-contact portion thereof. The liquid-contact portion is formed of a material selected from the group consisting of epoxy-phenolic resin, phenolic resin, phenolic-butyral resin, stainless steel, iron phosphate, zinc phosphate and glass.

The material of the liquid-contact portion may be selected from the group consisting of phenolic resin, phenolic-butyral resin, iron phosphate and zinc phosphate.

The material of the liquid-contact portion may be selected from the group consisting of iron phosphate and zinc phosphate.

The storage method of HCFO-1233zd (Z) may use the storage container in which the material of the liquid-contact portion is epoxy-phenolic resin.

The storage method of HCFO-1233zd (Z) may use the storage container in which the material of the liquid-contact portion is phenolic resin.

The storage method of HCFO-1233zd (Z) may use the storage container in which the material of the liquid-contact portion is phenolic-butyral resin.

The storage method of HCFO-1233zd (Z) may use the storage container in which the material of the liquid-contact portion is stainless steel.

The storage method of HCFO-1233zd (Z) may use the storage container in which the material of the liquid-contact portion is iron phosphate.

The storage method of HCFO-1233zd (Z) may use the storage container in which the material of the liquid-contact portion is zinc phosphate.

The storage method of HCFO-1233zd (Z) may use the storage container in which the material of the liquid-contact portion is glass.

The HCFO-1233zd (Z) may be stored in the storage container in a sealed manner.

AnHCFO-1233zd (Z) according to an embodiment of the present invention has a moisture content held at 50 ppm or lower after being stored for a predetermined time period.

The HCFO-1233zd (Z) may have a moisture content held at 20 ppm or lower after being stored for a predetermined time period.

The HCFO-1233zd (Z) may have an evaporation residue content held at 50 ppm or lower after being stored for a predetermined time period.

The HCFO-1233zd (Z) may have a purity held at 99.5% or higher after being stored for a predetermined time period.

The HCFO-1233zd (Z) may have an acid content held at 1 ppm or lower after being stored for a predetermined time period.

The HCFO-1233zd (Z) may have a Hazen color index held at 20 or lower after being stored for a predetermined time period.

The HCFO-1233zd (Z) may have a hue held as being colorless and transparent after being stored for a predetermined time period.

The HCFO-1233zd (Z) has been stored for a predetermined time period in a storage container. A liquid-contact portion of the storage container may be formed of a material selected from the group consisting of epoxy-phenolic resin, phenolic resin, phenolic-butyral resin, stainless steel, iron phosphate, zinc phosphate and glass.

The material of the liquid-contact portion may be selected from the group consisting of phenolic resin, phenolic-butyral resin, iron phosphate and zinc phosphate.

The material of the liquid-contact portion may be selected from the group consisting of iron phosphate and zinc phosphate.

An HCFO-1233zd (Z) product according to an embodiment of the present invention includes at least HCFO-1233zd (Z); and a storage container for HCFO-1233zd (Z) which is in direct contact with HCFO-1233zd (Z) as a liquid at a liquid-contact portion thereof. The liquid-contact portion is formed of a material selected from the group consisting of epoxy-phenolic resin, phenolic resin, phenolic-butyral resin, stainless steel, iron phosphate, zinc phosphate and glass.

The material of the liquid-contact portion may be selected from the group consisting of phenolic resin, phenolic-butyral resin, iron phosphate and zinc phosphate.

The material of the liquid-contact portion may be selected from the group consisting of iron phosphate and zinc phosphate.

The HCFO-1233zd (Z) product may include at least: HCFO-1233zd (Z); and a storage container for HCFO-1233zd (Z) which is in direct contact with HCFO-1233zd (Z) as a liquid at a liquid-contact portion thereof. The liquid-contact portion may be formed of epoxy-phenolic resin.

The liquid-contact portion may be formed of phenolic resin.

The liquid-contact portion may be formed of phenolic-butyral resin.

The liquid-contact portion may be formed of stainless steel.

The liquid-contact portion may be formed of iron phosphate.

The liquid-contact portion may be formed of zinc phosphate.

The liquid-contact portion may be formed of glass.

The storage container for HCFO-1233zd (Z) may be sealable.

DESCRIPTION OF EMBODIMENTS

Hereinafter, embodiments of the present invention will be described in detail. The storage container and the storage method of HCFO-1233zd (Z), stored HCFO-1233zd (Z) and HCFO-1233zd (Z) products in embodiments according to this disclosure may be provided in various different forms, and should not be construed as being limited to any of the following embodiments.

<How the Present Invention has been Achieved>

A long-term storage test of HCFO-1233zd (Z) was made. As shown in comparative example 1 to comparative example 3 in Table 1 provided below, HCFO-1233zd (Z) was stored at room temperature for 6 months in storage containers including liquid-contact portions respectively formed of tin-free steel, polymyte (registered trademark) and polyethylene. It was found that the moisture content or the evaporation residue content of HCFO-1233zd (Z) was conspicuously increased. HCFO-1233zd (Z), which is to be used as a solvent or a detergent, is required not to be decreased in performance even after being stored in a storage container for a predetermined time period. Namely, HCFO-1233zd (Z) is required not to be changed much in acid content, moisture content, purity, evaporation residue content, hue (Hazen color index) and the like after being stored in a storage container for a predetermined time period. Even if the value of merely one of the above-listed items is significantly changed after storage for a predetermined time period, HCFO-1233zd (Z) may cause a serious problem such as a cleaning defect or the like when being used as a detergent.

Based on such results, the present inventors made studies on a plurality of different types of storage containers including liquid-contact portions formed of different materials, as a storage container usable to be filled with HCFO-1233zd (Z).

EMBODIMENTS

A material usable for an inner surface of a storage container for HCFO-1233zd (Z) in an embodiment according to the present invention is a resin, an alloy or a coat that does not decrease the performance of HCFO-1233zd (Z) at a liquid-contact portion, which is to be in contact with HCFO-1233zd (Z). Such a material is, for example, selected from the group consisting of epoxy-phenolic resin, phenolic resin, phenolic-butyral resin, stainless steel, iron phosphate, zinc phosphate and glass. After being stored for a predetermined time period in a storage container using such a material for an inner surface, HCFO-1233zd (Z) does not much changed in acid content, moisture content, purity, evaporation residue content or hue (Hazen color index). These materials improve the rust resistance and the chemical resistance of a storage container. Therefore, a storage container formed of any of these materials maintains the quality of HCFO-1233zd (Z), and is usable to store and transport HCFO-1233zd (Z) safely and stably at low cost. Epoxy-phenolic resin, phenolic resin, stainless steel and phenolic-butyral resin may be used as a material of a container or a coat of a metal container. Alternatively, a composite container including a metal outer layer and an inner container formed of such a resin or alloy may be used. Iron phosphate and zinc phosphate may be used for a coat covering a liquid-contact portion of a container including a steel outer casing. Glass may be used for a glass container. A container formed of a metal plate lined with glass may be used.

The liquid-contact portion of the storage container for HCFO-1233zd (Z) in an embodiment according to the present invention may be formed of phenolic resin, phenolic-butyral resin, iron phosphate or zinc phosphate. Such a container is usable for stable storage and transportation at lower cost, and thus is more preferred as a storage container for HCFO-1233zd (Z). The storage container for HCFO-1233zd (Z) in an embodiment according to the present invention may be formed of steel (SPCC) and include a liquid-contact portion coated with iron phosphate or zinc phosphate. Such a container is usable for stable storage and transportation at lower cost, and thus is especially preferred.

The storage container for HCFO-1233zd (Z) in an embodiment according to the present invention is to be filled with HCFO-1233zd (Z), which is a liquid at room temperature. Such a storage container does not require any specific structure and may have any of a wide range of forms and functions. The storage container may be, for example, a storage tank as a fixed storage container, a 1 L glass bottle usable also for transportation, a 20 L pail, a 200 L drum or the like.

The storage container for HCFO-1233zd (Z) in an embodiment according to the present invention may be sealable. There is no specific limitation on the method for sealing the storage container for HCFO-1233zd (Z). The storage container may be sealed with a screw cap or a valve. Preferably, HCFO-1233zd (Z) is stored in an air-tight sealed storage container in order to be stored for a long time period without being deteriorated.

The material of the storage container in this embodiment is iron (steel), stainless steel or glass. There is no specific limitation on the thickness of an iron container. The lower limit of the thickness may be 0.3 mm, and is generally 0.34 mm. There is no specific upper limit of the thickness. The upper limit may be 80 mm, is generally 2 mm, and is preferably 1.6 mm. A stainless steel container may be formed of SUS316, SUS304 or JFE443CT. There is no specific limitation on the thickness of such a stainless steel container. The lower limit of the thickness may be 0.5 mm, and is generally 0.6 mm. There is no specific upper limit of the thickness. The upper limit may be 80 mm, is generally 5 mm, and is preferably 2.5 mm. A 20 L pail or a 200 L drum formed of iron (steel plate) or stainless steel preferably has a thickness of 0.6 mm to 1.6 mm in conformity with Japanese Industrial Standards (JIS Z 1620 "steel pail" or JIS Z 1601 "steel tight head drum"). The storage container is not restricted to any of the above as long as having durability sufficient for the purpose. For example, the container may be formed of carbon steel, manganese steel, chromium molybdenum steel, any other type of low ally steel, aluminum alloy or the like. There is no specific limitation on the thickness of a glass container. The thickness of a glass container may be 1.0 mm or greater, and there is no specific upper limit. The thickness may be 1.0 mm to 10 mm, and is preferably 1.6 mm to 5.0 mm.

The storage container in this embodiment may be bead-processed to be improved in durability.

The upper limit of the temperature at which HCFO-1233zd (Z) in an embodiment according to the present invention is stored is preferably 40° C. or lower, more preferably 35° C. or lower, and still more preferably 30° C. or lower from the point of view of safety. There is no specific limitation on the lower limit of the temperature at which HCFO-1233zd (Z) in an embodiment according to the present invention is stored. The lower limit is preferably −30° C. or higher, more preferably −15° C. or higher, and still more preferably 0° C. or higher. HCFO-1233zd (Z) may be stored in a refrigerator or the like, or may be stored in an environment with no refrigeration facilities in the case where HCFO-1233zd (Z) may be kept at a temperature of the above-mentioned upper limit at the highest.

Use of a storage container for HCFO-1233zd (Z) in an embodiment according to the present invention provides a storage method that maintains the quality of HCFO-1233zd (Z) and is usable to store and transport HCFO-1233zd (Z) safely and stably at low cost.

HCFO-1233zd (Z) stored in a storage container for HCFO-1233zd (Z) in an embodiment according to the present invention for a predetermined time period (e.g., 6 months) is characterized in having a moisture content held at 50 ppm or lower. More preferably, HCFO-1233zd (Z) has a moisture content held at 20 ppm or lower. The unit of the moisture content (ppm) is a mass ratio of moisture with respect to HCFO-1233zd (Z).

HCFO-1233zd (Z) stored in a storage container for HCFO-1233zd (Z) in an embodiment according to the present invention for a predetermined time period (e.g., 6 months) is characterized in having an evaporation residue content (amount of component left after HCFO-1233zd (Z) is evaporated) held at 50 ppm or lower. The unit of evaporation residue content (ppm) is a mass ratio of evaporation residue with respect to HCFO-1233zd (Z).

HCFO-1233zd (Z) stored in a storage container for HCFO-1233zd (Z) in an embodiment according to the present invention for a predetermined time period (e.g., 6 months) is characterized in having a purity held at 99.5% or higher. The unit of purity (%) is a peak area size ratio of HCFO-1233zd (Z) with respect to all the components. The peak area size ratio is calculated by an area percentage method by use of a gas chromatograph including a flame ionization detector (FID).

HCFO-1233zd (Z) stored in a storage container for HCFO-1233zd (Z) in an embodiment according to the present invention for a predetermined time period (e.g., 6 months) is characterized in having an acid content held at 1 ppm or lower. The unit of acid content (ppm) is a mass ratio of acid with respect to HCFO-1233zd (Z).

HCFO-1233zd (Z) stored in a storage container for HCFO-1233zd (Z) in an embodiment according to the present invention for a predetermined time period (e.g., 6 months) is characterized in having a hue that is colorless and transparent. HCFO-1233zd (Z) stored in a storage container for HCFO-1233zd (Z) in an embodiment according to the present invention for a predetermined time period (e.g., 6 months) is characterized in having a Hazen color index [APHA] held at 20 or lower. The Hazen color index is preferably 15 or lower, and is more preferably 10 or lower. The Hazen color index may be measured by a method designated in Japanese Industrial Standards K 0071-1 (test methods for color of chemical products) or by use of a commercially available spectrophotometer compliant to the above-mentioned standards.

A storage container for HCFO-1233zd (Z) in embodiment 1 according to the present invention is formed of iron (steel), and a liquid-contact portion thereof is formed of epoxy-phenolic resin. The iron container may have a thickness of 0.3 mm or greater, and there is no specific upper limit. The thickness may be 0.3 mm to 80 mm, is generally 0.34 mm to 2 mm, is preferably 0.34 mm to 1.6 mm, and is especially preferably 0.6 mm to 1.6 mm. The liquid-contact portion is formed of epoxy-phenolic resin. The liquid-contact portion may have a thickness of 3 μm or greater, and there is no specific upper limit. The thickness may be 3 μm to 30 μm, and is preferably 5 μm to 25 μm. Even after being stored in a storage container for HCFO-1233zd (Z) in embodiment 1 according to the present invention at room temperature or 35° C. for 6 months, HCFO-1233zd (Z) exhibits almost no change in acid content, moisture content, purity, evaporation residue content or hue. Therefore, such a storage container maintains the quality of HCFO-1233zd (Z), and is usable to store and transport HCFO-1233zd (Z) safely and stably at low cost.

In an embodiment according to the present invention, the epoxy-phenolic resin may be any of mixed resins of phenolic resin and epoxy resin described below. The phenolic resin may be a condensate derived from a phenolic compound by a conventionally known method. Examples of the phenolic compound include tetrafunctional phenols such as bisphenol A, bisphenol B, bisphenol F, 1,1-bis(4-hydroxyphenyl)ethane and the like; trifunctional phenols such as phenol (carbolic acid), m-cresol, m-ethylphenol, 3,5-xylenol, m-methoxyphenol, and the like; and bifunctional phenols such as o-cresol, p-cresol, p-tert-buthylphenol, p-ethylphenol, 2,3-xylenol, 2,5-xylenol, p-tert-aminophenol, p-nonylphenol, p-phenylphenol, p-cyclohexylphenol, and the like; etc. The phenolic compound is not limited to these. The epoxy resin may be a condensate derived from an epoxy compound by a conventionally known method. Examples of the epoxy compound include glycidyl ethers, glycidyl esters, glycidyl amines, linear aliphatic epoxides, alicyclic epoxides, hydantoin-type epoxides, and the like. The epoxy compound is not limited to these. In an embodiment according to the present invention, the epoxy-phenolic resin may be a resin including at least a phenolic structure and an epoxy structure.

Specific examples of the epoxy-phenolic resin include, for example, E-90-NSP produced by Toyo Ink Co., Ltd., Kancoat SJ-L6611 produced by Kansai Paint Co., Ltd., Eponics 1100 Clear produced by Dai Nippon Toryo Co., Ltd. (resin ratio:epoxy resin:phenolic resin=70%:30%), Neo Gose #1 Clear produced by Shinto Paint Co., Ltd. (resin ratio:epoxy resin:phenolic resin=80%:20%), SK-2059C produced by Sakuranomiya Chemical Co., Ltd. (resin ratio:epoxy resin:phenolic resin=60%:40%), and the like.

A storage container for HCFO-1233zd (Z) in embodiment 2 according to the present invention is formed of iron (steel), and a liquid-contact portion thereof is formed of phenolic resin. The iron container may have a thickness of 0.3 mm or greater, and there is no specific upper limit. The thickness may be 0.3 mm to 80 mm, is generally 0.34 mm to 2 mm, is preferably 0.34 mm to 1.6 mm, and is especially preferably 0.6 mm to 1.6 mm. The liquid-contact portion is formed of phenolic resin. The liquid-contact portion may have a thickness of 3 µm or greater, and there is no specific upper limit. The thickness may be 3 µm to 30 µm, and is preferably 5 µm to 25 µm. Even after being stored in a storage container for HCFO-1233zd (Z) in embodiment 2 according to the present invention at 35° C. for 6 months, HCFO-1233zd (Z) exhibits almost no change in acid content, moisture content, purity, evaporation residue content or hue. Therefore, such a storage container maintains the quality of HCFO-1233zd (Z), and is usable to store and transport HCFO-1233zd (Z) safely and stably.

In an embodiment according to the present invention, the phenolic resin may be a condensate derived from a phenolic compound by a conventionally known method. Examples of the phenolic compound include tetrafunctional phenols such as bisphenol A, bisphenol B, bisphenol F, 1,1-bis(4-hydroxyphenyl)ethane and the like; trifunctional phenols such as phenol (carbolic acid), m-cresol, m-ethylphenol, 3,5-xylenol, m-methoxyphenol, and the like; and bifunctional phenols such as o-cresol, p-cresol, p-tert-buthylphenol, p-ethylphenol, 2,3-xylenol, 2,5-xylenol, p-tert-aminophenol, p-nonylphenol, p-phenylphenol, p-cyclohexylphenol, and the like; etc. The phenolic compound is not limited to these.

Specific examples of the phenolic resin include, for example, E-500-4A produced by Toyo Ink Co., Ltd., E-526 produced by Toyo Ink Co., Ltd., Kancoat SJ-1518M produced by Kansai Paint Co., Ltd., and the like.

A storage container for HCFO-1233zd (Z) in embodiment 3 according to the present invention is formed of iron (steel), and a liquid-contact portion thereof is formed of phenolic-butyral resin. The iron container may have a thickness of 0.3 mm or greater, and there is no specific upper limit. The thickness may be 0.3 mm to 80 mm, is generally 0.34 mm to 2 mm, is preferably 0.34 mm to 1.6 mm, and is especially preferably 0.6 mm to 1.6 mm. The liquid-contact portion is formed of phenolic-butyral resin. The liquid-contact portion may have a thickness of 3 µm or greater, and there is no specific upper limit. The thickness may be 3 µm to 30 µm, and is preferably 5 µm to 25 µm. Even after being stored in a storage container for HCFO-1233zd (Z) in embodiment 3 according to the present invention at 35° C. for 6 months, HCFO-1233zd (Z) exhibits almost no change in acid content, moisture content, purity, evaporation residue content or hue. Therefore, such a storage container maintains the quality of HCFO-1233zd (Z), and is usable to store and transport HCFO-1233zd (Z) safely and stably.

In an embodiment according to the present invention, the phenolic-butyral resin may be any of mixed resins of any of the above-mentioned phenolic resins and butyral resin (PVB). The phenolic-butyral resin may be a resin including at least a phenolic structure and a vinylbutyral structure.

Specific examples of the phenolic-butyral resin include, for example, E-318-1 produced by Toyo Ink Co., Ltd. (resin ratio:phenolic resin:butyral resin=87%:13%), and the like.

A storage container for HCFO-1233zd (Z) in embodiment 4 according to the present invention is formed of stainless steel. The stainless steel container may have a thickness of 0.5 mm or greater, and there is no specific upper limit. The thickness may be 0.5 mm to 80 mm, is generally 0.6 mm to 5 mm, and is preferably 0.6 mm to 2.5 mm. Even after being stored in a storage container for HCFO-1233zd (Z) in embodiment 4 according to the present invention at 35° C. for 6 months, HCFO-1233zd (Z) exhibits almost no change in acid content, moisture content, purity, evaporation residue content or hue. Therefore, such a storage container maintains the quality of HCFO-1233zd (Z), and is usable to store and transport HCFO-1233zd (Z) safely and stably.

A storage container for HCFO-1233zd (Z) in embodiment 5 according to the present invention is formed of iron (steel), and a liquid-contact portion thereof is formed of an iron phosphate-based coat. The iron container may have a thickness of 0.3 mm or greater, and there is no specific upper limit. The thickness may be 0.3 mm to 80 mm, is generally 0.34 mm to 2 mm, is preferably 0.34 mm to 1.6 mm, and is especially preferably 0.6 mm to 1.6 mm. The liquid-contact portion is formed of an iron phosphate-based coat having a composition represented by chemical formula $FePO_4 \cdot 2H_2O$. The liquid-contact portion generally has a thickness of 1 µm or less, and may have a thickness of 0.5 µm or less. Even after being stored in a storage container for HCFO-1233zd (Z) in embodiment 5 according to the present invention at 35° C. for 6 months, HCFO-1233zd (Z) exhibits almost no change in acid content, moisture content, purity, evaporation residue content or hue. Therefore, such a storage container maintains the quality of HCFO-1233zd (Z), and is usable to store and transport HCFO-1233zd (Z) safely and stably.

A storage container for HCFO-1233zd (Z) in embodiment 6 according to the present invention is formed of iron (steel), and a liquid-contact portion thereof is formed of a zinc phosphate-based coat. The iron container may have a thickness of 0.3 mm or greater, and there is no specific upper limit. The thickness may be 0.3 mm to 80 mm, is generally 0.34 mm to 2 mm, is preferably 0.34 mm to 1.6 mm, and is especially preferably 0.6 mm to 1.6 mm. The liquid-contact portion is formed of a zinc phosphate-based coat having a composition represented by chemical formula $Zn_3(PO_4)_2 \cdot 4H_2O$ or $Zn_2Fe(PO_4)_2 \cdot 4H_2O$. The liquid-contact portion generally has a thickness of 5 µm or less, and preferably has a thickness of 3 µm to 5 µm. Even after being stored in a storage container for HCFO-1233zd (Z) in embodiment 6 according to the present invention at 35° C. for 6 months, HCFO-1233zd (Z) exhibits almost no change in acid content, moisture content, purity, evaporation residue content or hue. Therefore, such a storage container maintains the quality of HCFO-1233zd (Z), and is usable to store and transport HCFO-1233zd (Z) safely and stably.

A storage container for HCFO-1233zd (Z) in embodiment 7 according to the present invention is formed of glass, and a liquid-contact portion thereof is formed of glass. The glass container may have a thickness of 1.0 mm or greater, and there is no specific upper limit. The thickness may be 1.0 mm to 10 mm, and is preferably 1.6 mm to 5.0 mm. Even after being stored in a storage container for HCFO-1233zd (Z) in embodiment 7 according to the present invention at 35° C. for 6 months, HCFO-1233zd (Z) exhibits almost no change in acid content, moisture content, purity, evaporation residue content or hue. Therefore, such a storage container maintains the quality of HCFO-1233zd (Z), and is usable to store and transport HCFO-1233zd (Z) safely and stably.

In an embodiment according to the present invention, the iron (steel) container or the stainless steel container in the above-described embodiments may include a welded portion. There is no specific limitation on the material of the welded portion. In the case where the welded portion is exposed to the surface of the container (in the case where the welded portion may be in contact with Z-1-chloro-3,3,3-trifluoropropene as a liquid), it is preferred that the welded portion is formed of a material that is the same as any one of the materials described above as being usable for the liquid-contact portion. There is no specific limitation on the method of welding the container. The storage container according to the present invention is preferably air-tight. Therefore, the welding method is preferably resistance welding, and especially preferably seam welding.

The present invention provides a storage container and a storage method that maintain the quality of Z-1-chloro-3,3,3-trifluoropropene (abbreviation: HCFO-1233zd (Z)) as a solvent or a detergent, and are usable to store and transport Z-1-chloro-3,3,3-trifluoropropene safely and stably at low cost.

EXAMPLES

Hereinafter, the present invention will be described by way of examples. The present invention is not limited to any of the examples.

Example 1

In this example, an iron (SPCC) container having an inner capacity of 19800 $cm^3$ (20C-285T-100810 produced by Daikan Corp.) was used as a storage container main body. The iron container has a thickness of 0.8 mm (body) and 1.0 mm (top and bottom). The liquid-contact portion is formed of epoxy-phenolic resin (E-90-NSP produced by Toyo Ink Co., Ltd.) and has a thickness of about 5 µm. About 2 kg of HCFO-1233zd (Z) (purity: 99.97%) was put into the storage container for HCFO-1233zd (Z), and the storage container was closed with a screw cap. HCFO-1233zd (Z) was kept still at room temperature for 6 months.

Comparative Example 1

In this comparative example, a tin-free steel container having an inner capacity of 19800 $cm^3$ was used as a storage container main body. The tin-free steel container has a thickness of 0.8 mm (body) and 1.0 mm (top and bottom). About 2 kg of HCFO-1233zd (Z) (purity: 99.97%) was put into the storage container for HCFO-1233zd (Z), and the storage container was closed with a screw cap. HCFO-1233zd (Z) was kept still at room temperature for 6 months.

Comparative Example 2

In this comparative example, an iron (SPCC) container having an inner capacity of 19800 $cm^3$ was used as a storage container main body. The iron container has a thickness of 0.8 mm (body) and 1.0 mm (top and bottom). The liquid-contact portion is formed of polymyte and has a thickness of 200 µm or greater. About 2 kg of HCFO-1233zd (Z) (purity: 99.97%) was put into the storage container for HCFO-1233zd (Z), and the storage container was closed with a screw cap. HCFO-1233zd (Z) was kept still at room temperature for 6 months.

Comparative Example 3

In this comparative example, an iron (SPCC) container having an inner capacity of 19800 $cm^3$ was used as a storage container main body. The iron container has a thickness of 0.8 mm (body) and 1.0 mm (top and bottom). The liquid-contact portion is formed of polyethylene and has a thickness of 0.1 mm or greater. About 2 kg of HCFO-1233zd (Z) (purity: 99.97%) was put into the storage container for HCFO-1233zd (Z), and the storage container was closed with a screw cap. HCFO-1233zd (Z) was kept still at room temperature for 6 months.

In the example and the comparative examples, various measurements were performed by the following methods.

(1) Acid Content

The acid content of HCFO-1233zd (Z) was calculated in accordance with the following procedure by use of a multiparameter water quality meter (device: MM-60R produced by DKK-Toa Corporation; electrode: GST-5741C produced by DKK-Toa Corporation).

About 0.0050 g of 0.5 N HCl (18.23 g/L) was put into a 100 mL polyethylene wide-mouth bottle and diluted with super pure water to about 100 g to obtain 1 ppm HCl.

About 25 g of 1 ppm HCl prepared by the above-described method was put into a 100 mL polyethylene wide-mouth bottle and diluted with super pure water to about 50 g to obtain 0.5 ppm HCl.

About 5 g of 1 ppm HCl was diluted with super pure water to about 50 g to obtain 0.1 ppm HCl by substantially the same method.

1 ppm, 0.5 ppm and 0.1 ppm HCl prepared above were subjected to a pH value measurement while being stirred by a stirrer.

A calibration curve was created by log approximation based on the obtained measurement results.

About 100 g of HCFO-1233zd (Z) in each of the example and the comparative examples and about 100 g of super pure water were put into a 250 mL polyethylene container and extracted, and a water layer was recovered by a PFA separatory funnel. Thus, sample liquids were obtained.

Each of the sample liquids was subjected to a pH value measurement while being stirred by a stirrer.

The acid content of HCFO-1233zd (Z) in each of the example and the comparative examples was calculated based on the obtained results by use of the calibration curve.

(2) Moisture Content

The moisture content of HCFO-1233zd (Z) in each of the example and the comparative examples was measured by use of a Karl Fischer moisture meter (device: MKC-710 produced by Kyoto Electronics Manufacturing Co., Ltd.).

(3) Purity

The purity of HCFO-1233zd (Z) in each of the example and the comparative examples was measured by gas chromatography (device: GC-2010 (produced by Shimadzu Corporation); detector: FID)).

(4) Evaporation Residue Content

The evaporation residue content of each of the samples was measured in accordance with the following procedure.

A 300 mL beaker was dried for 1 hour by a dryer at 100° C. and the temperature thereof was lowered to room temperature by a desiccator containing silica gel (blue).

The beaker was weighed accurately (twice).

HCFO-1233zd (Z) in each of the example and the comparative examples was sampled in an amount of 200 mL by a 200 mL graduated cylinder with a sealing lid, and weighed.

The above-described beaker containing a stirrer was put on a hot plate, with a stirrer, set at 100° C., and 100 mL of each of the samples was put into the beaker and evaporated at a stirring rate of 200 rpm.

When the weight of the sample was decreased by a certain degree, the remaining 100 mL of the sample was added.

When the amount of the sample was decreased to about 50 mL, the stirrer was removed and the evaporation was continued until the beaker was emptied.

After the sample was evaporated completely, the beaker was put into a desiccator and left for an hour, and then weighed accurately (twice).

(5) Hue

The color of HCFO-1233zd (Z) in each of example 1 and comparative example 1 to comparative example 3 was visually observed. A colorless and transparent sample was evaluated as "○", and a colored sample (specifically, a pale yellow sample) was evaluated as "x".

The analysis results on the acid content, moisture content, purity, evaporation residue content and hue of example 1 and comparative example 1 to comparative example 3 are shown in Table 1. The analysis results on the acid content, moisture content, purity, evaporation residue content and hue of pre-storage HCFO-1233zd (Z) (purity: 99.97%) are shown in Table 1.

TABLE 1

| Number | The material of the liquid-contact portion | Acid content (ppm) | Moisture content (ppm) | Purity (%) | Evaporation residue content (ppm) | Hue (—) |
|---|---|---|---|---|---|---|
| pre-storage | — | 0.1 | 23 | 99.97 | <1 | ○ |
| Example 1 | Epoxy-phenolic resin | 0.1 | 46 | 99.96 | 10 | ○ |
| Comparative example 1 | Tin-free | 0.1 | 176 | 99.96 | 22 | ○ |
| Comparative example 2 | Polymyte | 0.1 | 71 | 99.96 | 248 | ○ |
| Comparative example 3 | Polyethylene | 0.1 | 256 | 99.97 | 2 | ○ |

In comparative example 1 and comparative example 3, the moisture content was recognized to be conspicuously increased. In comparative example 2, the evaporation residue content was recognized to be conspicuously increased. By contrast, in example 1, the post-test change in each of the acid content, moisture content, purity, and evaporation residue content of HCFO-1233zd (Z) was within the margin of error. No significant change was recognized.

Example 2

In this example, an iron (SPCC) container having an inner capacity of 19800 cm$^3$ (20C-285T-100810 produced by Daikan Corp.) was used as a storage container main body. The iron container has a thickness of 0.8 mm (body) and 1.0 mm (top and bottom). The liquid-contact portion is formed of epoxy-phenolic resin (E-90-NSP produced by Toyo Ink Co., Ltd.) and has a thickness of about 5 μm. About 2 kg of HCFO-1233zd (Z) (purity: 99.97%) was put into the storage container for HCFO-1233zd (Z), and the storage container was closed with a screw cap. HCFO-1233zd (Z) was kept still at 35° C. for 6 months.

Example 3

In this example, an iron (SPCC) container having an inner capacity of 19800 cm$^3$ (20C-285T-100810 produced by Daikan Corp.) was used as a storage container main body. The iron container has a thickness of 0.8 mm (body) and 1.0 mm (top and bottom). The liquid-contact portion is formed of phenolic resin (Kancoat SJ-1518M produced by Kansai Paint Co., Ltd.) and has a thickness of about 5 μm. About 2 kg of HCFO-1233zd (Z) (purity: 99.97%) was put into the storage container for HCFO-1233zd (Z), and the storage container was closed with a screw cap. HCFO-1233zd (Z) was kept still at 35° C. for 6 months.

Example 4

In this example, an iron (SPCC) container having an inner capacity of 19800 cm$^3$ (20C-285T-100810 produced by Daikan Corp.) was used as a storage container main body. The iron container has a thickness of 0.8 mm (body) and 1.0 mm (top and bottom). The liquid-contact portion is formed of phenolic-butyral resin (E-318-1 produced by Toyo Ink Co., Ltd.) and has a thickness of about 5 μm. About 2 kg of HCFO-1233zd (Z) (purity: 99.97%) was put into the storage container for HCFO-1233zd (Z), and the storage container was closed with a screw cap. HCFO-1233zd (Z) was kept still at 35° C. for 6 months.

Example 5

In this example, a stainless steel (SUS304) container having an inner capacity of 100 L (A-3170 produced by Wada Stainless Industry Co., Ltd.) was used as a storage container main body. The stainless steel container has a thickness of 2.0 mm. The liquid-contact portion is formed of SUS304. About 10 kg of HCFO-1233zd (Z) (purity: 99.97%) was put into the storage container for HCFO-1233zd (Z), and the storage container was closed with a ball valve. HCFO-1233zd (Z) was kept still at 35° C. for 6 months.

[Measurement Method]

The acid content, moisture content, purity and evaporation residue content were measured by a method substantially the same as that described above, and the measuring method will not be described in detail. In these examples, the Hazen color index [APHA] was measured by the following method.

(6) Hazen color index [APHA]

The Hazen color index [APHA] of each of the samples was measured in accordance with the following procedure.

The Hazen color index [APHA] of HCFO-1233zd (Z) in each of the examples were measured by use of a spectrophotometer (device: TZ6000 produced by Nippon Denshoku Industries Co., Ltd.).

The analysis results on the acid content, moisture content, purity, evaporation residue content and Hazen color index of example 2 to example 5 are shown in Table 2. The analysis results on the acid content, moisture content, purity, evaporation residue content and Hazen color index of pre-storage HCFO-1233zd (Z) (purity: 99.97%) are shown in Table 2.

TABLE 2

| Number | The material of the liquid-contact portion | Acid content (ppm) | Moisture content (ppm) | Purity (%) | Evaporation residue content (ppm) | Hazen color index (APHA) |
|---|---|---|---|---|---|---|
| pre-storage | — | 0.1 | 4 | 99.97 | <1 | 3 |
| Example 2 | Epoxy-phenolic resin | 0.1 | 19 | 99.97 | 10 | 5 |
| Example 3 | Phenolic resin | 0.1 | 34 | 99.97 | 6 | 8 |
| Example 4 | Phenolic-butyral resin | 0.1 | 25 | 99.97 | 9 | 11 |
| Example 5 | SUS304 | 0.1 | 7 | 99.97 | 3 | 2 |

In any of the examples, the post-test change in each of the acid content, moisture content, purity, evaporation residue content and Hazen color index of HCFO-1233zd (Z) was within the margin of error. No significant change was recognized.

A test was performed in which HCFO-1233zd (Z) was stored in substantially the same manner as in example 2 to example 5 at a temperature lower than 35° C. (e.g., about 5° C., about 20° C.) for 6 months or 12 months. In such a case also, like in example 2 to example 5, the post-test change in each of the acid content, moisture content, purity, evaporation residue content and Hazen color index of HCFO-1233zd (Z) was within the margin of error. No significant change was recognized.

Example 6

In this example, an iron (SPCC) container having an inner capacity of 19800 cm$^3$ (20C-285T-100810 produced by Daikan Corp.) was used as a storage container main body. The iron container has a thickness of 0.8 mm (body) and 1.0 mm (top and bottom). The liquid-contact portion is formed of epoxy-phenolic resin (E-90-NSP produced by Toyo Ink Co., Ltd.) and has a thickness of about 5 µm. About 22 kg of HCFO-1233zd (Z) (purity: 99.97%) was put into the storage container for HCFO-1233zd (Z), and the storage container was closed with a screw cap. HCFO-1233zd (Z) was kept still at 35° C. for 6 months.

Example 7

In this example, a stainless steel (SUS304) container having an inner capacity of 19800 cm$^3$ (20S-285T-A0.6 produced by Daikan Corp.) was used as a storage container main body. The stainless steel container has a thickness of 0.6 mm (body, top and bottom). The liquid-contact portion is formed of SUS304. About 22 kg of HCFO-1233zd (Z) (purity: 99.97%) was put into the storage container for HCFO-1233zd (Z), and the storage container was closed with a screw cap. HCFO-1233zd (Z) was kept still at 35° C. for 6 months.

Example 8

In this example, an iron (SPCC) container having an inner capacity of 19800 cm$^3$ (20C-285T-100810 produced by Daikan Corp.) was used as a storage container main body. The iron container has a thickness of 0.8 mm (body) and 1.0 mm (top and bottom). The liquid-contact portion is formed of an iron phosphate-based coat having a composition represented by chemical formula $FePO_4.2H_2O$. The iron phosphate-based coat has a thickness of 1 µm or less. About 22 kg of HCFO-1233zd (Z) (purity: 99.97%) was put into the storage container for HCFO-1233zd (Z), and the storage container was closed with a screw cap. HCFO-1233zd (Z) was kept still at 35° C. for 6 months.

Example 9

In this example, an iron (SPCC) container having an inner capacity of 19800 cm$^3$ (produced by Daikan Corp.) was used as a storage container main body. The iron container has a thickness of 0.6 mm (body, top and bottom). The liquid-contact portion is formed of a zinc phosphate-based coat having a composition represented by chemical formula $Zn_3(PO_4)_2.4H_2O$ or $Zn_2Fe(PO_4)_2.4H_2O$. The zinc phosphate-based coat has a thickness of 5 µm or less. About 22 kg of HCFO-1233zd (Z) (purity: 99.97%) was put into the storage container for HCFO-1233zd (Z), and the storage container was closed with a screw cap. HCFO-1233zd (Z) was kept still at 35° C. for 6 months.

Example 10

In this example, a brown glass container having an inner capacity of 1100 cm$^3$ (BGB1100A produced by Toyo Glass Co., Ltd.) was used as a storage container main body. The brown glass container has a thickness of 1.6 mm or greater (body) and 3.5 mm or greater (bottom). The liquid-contact portion is formed of glass. About 1 kg of HCFO-1233zd (Z) (purity: 99.97%) was put into the storage container for HCFO-1233zd (Z), and the storage container was closed with a screw cap. HCFO-1233zd (Z) was kept still at 35° C. for 6 months.

The analysis results on the acid content, moisture content, purity, evaporation residue content and Hazen color index of example 6 to example 10 are shown in Table 3. The analysis results on the acid content, moisture content, purity, evaporation residue content and Hazen color index of pre-storage HCFO-1233zd (Z) (purity: 99.97%) are shown in Table 3.

TABLE 3

| Number | The material of the liquid-contact portion | Acid content (ppm) | Moisture content (ppm) | Purity (%) | Evaporation residue content (ppm) | Hazen color index (APHA) |
|---|---|---|---|---|---|---|
| pre-storage | — | <0.1 | 6 | 99.97 | <1 | 3 |
| Example 6 | Epoxy-phenolic resin | <0.1 | 6 | 99.98 | 1 | 4 |
| Example 7 | SUS304 | <0.1 | 4 | 99.98 | <1 | 3 |
| Example 8 | Iron phosphate | <0.1 | 6 | 99.98 | 3 | 5 |
| Example 9 | Zinc phosphate | <0.1 | 8 | 99.98 | 3 | 3 |
| Example 10 | Glass | <0.1 | 7 | 99.98 | <1 | 3 |

In any of the examples, the post-test change in each of the acid content, moisture content, purity, evaporation residue content and Hazen color index of HCFO-1233zd (Z) was within the margin of error. No significant change was recognized. In all the examples, HCFO-1233zd (Z) maintained a colorless and transparent external appearance.

A test was performed in which HCFO-1233zd (Z) was stored in substantially the same manner as in example 6 to example 10 at a temperature lower than 35° C. (e.g., about 5° C., about 20° C.) for 6 months or 12 months. In such a case also, like in example 6 to example 10, the post-test change in each of the acid content, moisture content, purity, evaporation residue content and Hazen color index of HCFO-1233zd (Z) was within the margin of error. No significant change was recognized.

The present invention is not limited to any of the above embodiments, and may be appropriately modified without departing from the gist thereof.

What is claimed is:

1. A storage method of cis-1-chloro-3,3,3-trifluoropropene (HCFO-1233zd (Z)), comprising: using a storage container having a liquid-contact portion thereof, wherein the liquid-contact portion is formed of a material selected from the group consisting of epoxy-phenolic resin, phenolic resin, phenolic-butyral resin, iron phosphate, and zinc phosphate.

2. The storage method of HCFO-1233zd (Z) according to claim 1, wherein the material of the liquid-contact portion is selected from the group consisting of phenolic resin, phenolic-butyral resin, iron phosphate and zinc phosphate.

3. The storage method of HCFO-1233zd (Z) according to claim 2, wherein the material of the liquid-contact portion is selected from the group consisting of iron phosphate and zinc phosphate.

4. The storage method of HCFO-1233zd (Z) according to claim 1, wherein the HCFO-1233zd (Z) is stored in the storage container in a sealed manner.

5. Cis-1-chloro-3,3,3-trifluoropropene (HCFO-1233zd (Z)), having a moisture content held at 50 ppm or lower in an analysis after being stored for 6 months in a storage container in which a liquid-contact portion thereof is formed of a material selected from the group consisting of epoxy-phenolic resin, phenolic resin, phenolic-butyral resin, iron phosphate, and zinc phosphate.

6. The HCFO-1233zd (Z) according to claim 5, having an evaporation residue content held at 50 ppm or lower in an analysis after being stored for 6 months in the storage container.

7. The HCFO-1233zd (Z) according to claim 5, having a purity held at 99.5% or higher in an analysis after being stored for 6 months in the storage container.

8. The HCFO-1233zd (Z) according to claim 5, having an acid content held at 1 ppm or lower in an analysis after being stored for 6 months in the storage container.

9. The HCFO-1233zd (Z) according to claim 5, having a Hazen color index held at 20 or lower in an analysis after being stored for 6 months in the storage container.

10. The HCFO-1233zd (Z) according to claim 5, having a hue held as being colorless and transparent in an analysis after being stored for 6 months in the storage container.

11. The HCFO-1233zd (Z) according to claim 5, wherein the material of the liquid-contact portion is selected from the group consisting of phenolic resin, phenolic-butyral resin, iron phosphate and zinc phosphate.

12. The HCFO-1233zd (Z) according to claim 11, wherein the material of the liquid-contact portion is selected from the group consisting of iron phosphate and zinc phosphate.

13. A cis-1-chloro-3,3,3-trifluoropropene (HCFO-1233 zd (Z)) product, comprising at least:
   HCFO-1233zd (Z); and
   a storage container for HCFO-1233zd (Z) being in direct contact with HCFO-1233zd (Z) as a liquid at a liquid-contact portion thereof,
   wherein the liquid-contact portion is formed of a material selected from the group consisting of epoxy-phenolic resin, phenolic resin, phenolic-butyral resin, iron phosphate, zinc phosphate.

14. The HCFO-1233zd (Z) product according to claim 13, wherein the material of the liquid-contact portion is selected from the group consisting of phenolic resin, phenolic-butyral resin, iron phosphate and zinc phosphate.

15. The HCFO-1233zd (Z) product according to claim 14, wherein the material of the liquid-contact portion is selected from the group consisting of iron phosphate and zinc phosphate.

16. The HCFO-1233zd (Z) product according to claim 15, wherein the storage container for HCFO-1233zd (Z) is sealable.

* * * * *